United States Patent [19]

Mikumo et al.

[11] Patent Number: 5,779,864
[45] Date of Patent: Jul. 14, 1998

[54] APPARATUS FOR ADJUSTING SECTIONAL AREA RATIO OF METAL-COVERED ELECTRIC WIRE

[75] Inventors: Akira Mikumo; Kenichi Takahashi; Masanobu Koganeya, all of Osaka, Japan

[73] Assignee: Sumitomo Electric Industries, Ltd., Japan

[21] Appl. No.: 746,518

[22] Filed: Jan. 28, 1997

Related U.S. Application Data

[62] Division of Ser. No. 599,454, Jan. 22, 1996, Pat. No. 5,602,488, which is a division of Ser. No. 189,404, Jan. 31, 1994, Pat. No. 5,507,924.

[30] Foreign Application Priority Data

| Feb. 1, 1993 | [JP] | Japan | 5-14734 |
| Mar. 29, 1993 | [JP] | Japan | 5-69734 |
| Jan. 19, 1994 | [JP] | Japan | 6-4147 |

[51] Int. Cl.$^6$ ............... C25D 17/00; C25F 7/00
[52] U.S. Cl. ............ 204/207; 204/211; 204/224 M; 204/225
[58] Field of Search ............ 204/206, 207–211, 204/224 R, 224 M, 225

[56] References Cited

U.S. PATENT DOCUMENTS 4,808,276  2/1989  Lefebvre et al. ............ 204/211 X

FOREIGN PATENT DOCUMENTS

| A-0 380 115 | 8/1990 | European Pat. Off. |
| A-2 556 830 | 6/1985 | France |
| A-3041552 | 10/1982 | Germany |
| A-2021 775 | 12/1979 | United Kingdom |

Primary Examiner—Donald R. Valentine
Attorney, Agent, or Firm—Pennie & Edmonds LLP

[57] ABSTRACT

Disclosed herein are methods of measuring, adjusting and uniformalizing a sectional area ratio of a metal-covered electric wire, a method of cleaning an electric wire, a method of manufacturing a metal-covered electric wire, an apparatus for measuring a sectional area ratio of a metal-covered electric wire, and an apparatus for electropolishing a metal-covered electric wire.

Electric resistance values of first and second materials are previously stored respectively so that a sectional area ratio of a metal-covered electric wire is calculated on the basis of the as-stored values and an actually measured electric resistance value of the metal-covered electric wire. Measurement and uniformalization of a sectional area ratio of a metal-covered electric wire and cleaning of an electric wire are carried out by dissolving surface layer parts of the electric wires by electropolishing.

1 Claim, 15 Drawing Sheets

APPARATUS FOR ADJUSTING SECTIONAL AREA RATIO OF METAL-COVERED ELECTRIC WIRE

This is a division of prior application Ser. No. 08/599,454 filed on Jan. 22, 1996, now U.S. Pat. No. 5,602,488 which is a divisional application Ser. No. 08/189,404, now U.S. Pat. No. 5,507,924 filed on Jan. 31, 1994.

BACKGROUND OF THE INVENTION

1. Field of the Invention

The present invention relates to methods of measuring, adjusting and uniformalizing a sectional area ratio of a metal-covered electric wire, a method of cleaning an electric wire, a method of manufacturing a metal-covered electric wire, an apparatus for measuring a sectional area ratio of a metal-covered electric wire and an apparatus for electropolishing a metal-covered electric wire, and more particularly, it relates to a method of measuring, in a nondestructive manner, a sectional area ratio between a first material part and a second material part of a metal covered electric wire having a core part including the first material and a metal covering layer formed of the second material covering the core part, a method of adjusting the sectional area ratio by electropolishing and a method of uniformalizing the sectional area along the longitudinal direction, a method of cleaning a surface layer part of an electric wire having a metal surface by electropolishing, a method of manufacturing a metal-covered electric wire by electropolishing, an apparatus for measuring a sectional area ratio of a metal-covered electric wire in a nondestructive manner, and an electropolishing apparatus for dissolving a surface layer part of a metal-covered electric wire by electropolishing.

2. Description of the Background Art

Among metal-covered electric wires having core parts which are covered with metal covering layers, a metal superconducting wire such as a Cu-covered NbTi superconducting wire, for example, is formed by a stabilizing material of copper or a copper alloy and a superconducting material embedded therein for attaining circuit protection upon breakage of its superconducting state.

In that case, a wire having single core includes a core part consisting only of a superconducting material, and a covering layer formed of copper or copper alloy. Meanwhile, a wire having multiple cores includes a core part consisting of a superconducting material embedded in a stabilizing material, and a covering layer covering the core part.

A superconducting wire of such a structure is generally manufactured in the following manner, for example:

FIG. 13 is a flow chart showing steps of manufacturing an NbTi superconducting single-core wire. FIGS. 14 to 16 illustrate respective stages in the steps of manufacturing the NbTi superconducting single-core wire. Among these figures, FIGS. 14 and 16 are perspective views, and FIG. 15 is a sectional view.

Referring to FIGS. 13 and 14, an NbTi alloy rod 1 is prepared from a raw material and charged in a hollow cylindrical copper pipe 3 for serving as a stabilizing material for the single-core wire, and the copper pipe 3 is evacuated with a copper cover 5, and sealed by electron beam welding. A superconducting composite obtained in this manner is called a billet. This billet has a section which is substantially similar to that of the final single core wire.

Referring to FIG. 15, the wire diameter of this billet 7 is reduced to 50 to 30% through an extruder 9.

Referring to FIG. 16, an extruded body 11 as obtained is further reduced to a final wire diameter through a wire draw bench 13.

Then, the surface of the superconducting wire as obtained is cleaned. This step is generally carried out by acid cleaning for chemically dissolving the surface. In more concrete terms, the acid cleaning is performed by setting a vessel containing acid in a line having supply and take-up mechanisms and passing the wire through the line for continuously dipping the same in the acid, thereby dissolving its surface. The current amount of dissolution is adjusted by strength of the acid and a time for dipping the wire in the acid (length of the vessel and the wire speed through the line). The acid as employed is prepared from sulfuric acid for a Cu-covered superconducting wire, for example.

After the aforementioned cleaning, a single-core superconducting wire is obtained.

FIG. 17 is a flow chart showing steps of manufacturing an NbTi superconducting multicore wire. FIG. 18 is a perspective view showing a stage in the steps of manufacturing an NbTi superconducting multicore wire.

Referring to FIGS. 17 and 18, single-core wires 15 are formed into hexagonal sections through a die, cut and cleaned, and then a required number of such single-core wires 15 are simultaneously charged in a copper pipe 3, which in turn is covered evacuated with a copper cover 5 and sealed by electron beam welding, to manufacture a multicore billet.

Then, this billet is passed through an extruder similarly to the case of manufacturing a single-core wire, repeatedly wire-drawn and heat treated, and subjected to stranding and the like, to obtain a multicore superconducting wire.

In a Cu-covered superconducting wire as obtained, a sectional area ratio (Cu/SC sectional area ratio) of Cu or a Cu alloy to a superconducting material such as NbTi is generally called a copper ratio. This copper ratio, which is an important characteristic value showing stability of the superconducting wire, is finely specified in relation to application of the superconducting wire.

In general, this copper ratio, i.e., the Cu/SC sectional area ratio, is measured in the following manner, for example:

First, an end portion of a Cu composite superconducting wire is sampled and its weight is measured. Then, a stabilizing material part of Cu or a Cu alloy is removed from the Cu-covered superconducting wire, and the weight of the remaining superconducting material part is measured. The Cu/SC sectional area ratio is obtained from the total weight and the weight of the superconducting material part of the as-sampled Cu-covered superconducting wire by calculation.

On the other hand, this copper ratio is adjusted as follows: A superconducting composite called a billet can be regarded as having a section which is similar to that of the final target superconducting wire. Therefore, the thickness of a copper pipe and the amount of a superconducting material to be charged therein are adjusted to be equal to the final target copper ratio in manufacturing of the billet.

However, the aforementioned manufacturing of a superconducting wire has the following various problems:

When the copper ratio of a superconducting wire is measured by a conventional method, only a Cu/SC sectional area ratio in an end of a Cu-covered superconducting wire can be measured since the target portion is sampled and measured in a destructive manner.

When the Cu/SC sectional area is measured by such a conventional method in quality control of a Cu-covered superconducting wire as manufactured, for example. the overall CU-covered superconducting wire must be cut and removed if a value measured at its end portion is not in an allowable range. Thus. the yield is deteriorated in this case. In particular, the Cu/SC sectional area ratio is easily fluctuated at an end portion of a Cu-covered superconducting wire, and hence it has been regarded as problematic to estimate the Cu/SC sectional area of the overall Cu-covered superconducting wire from the value measured at the end portion. Therefore. dispersion of the copper ratio has been generally recognized through a destructive test along the overall length in an experiment, while such recognition cannot be applied to product inspection. Thus, the copper ratio in the middle of wire product cannot be measured.

In order to adjust the copper ratio of a superconducting wire by a conventional method, further, the copper ratio must be decided in manufacturing of a billet since only a sectional structure which is similar to that of the target wire is obtained by degressive working. Namely, it is necessary to manufacture billets having different copper ratios in order to manufacture superconducting wires having different copper ratios, and hence the manufacturing steps are complicated.

When a surface of an electric wire is cleaned or foreign matters are removed from the surface by a conventional method, on the other hand, the following problem arises: Namely, uniform dissolution cannot be attained in the conventional acid cleaning, since the dissolving power of the acid is reduced with cleaning. Further, an extremely long time is required for carrying out the dissolution which is required for removing foreign matters, due to insufficiency in absolute amount of surface dissolution in the same time.

When a superconducting wire is manufactured by a conventional method, in addition, ununiform deformation of the material is caused in a die applying a high pressure particularly when a billet is extruded, to cause dispersion in copper ratio of the as-manufactured superconducting wire.

It is assumed that such dispersion in copper ratio is caused in the following mechanism:

FIGS. 19 to 21 are sectional views showing states of a superconducting wire in extrusion.

When a billet comprising a core part 17, consisting of a superconducting material embedded in copper serving as stabilizing material which is covered with a copper cover portion 19 is extruded along arrow 23 through an extrusion die 21 as shown in FIG. 19, the copper cover portion 19 cannot satisfactorily flow with the core part 17 in the extrusion die 21 in an initial stage of extrusion, due to difference in strength and positional relation between the core part 17 and the copper cover portion 19.

Therefore, the copper cover portion 19 is rearwardly fed as if the same is scraped, as shown in FIG. 20.

Thereafter the rearwardly fed copper remains independently of the core part 17, to disadvantageously define the so-called bank 25, as shown in FIG. 21.

FIG. 22 is a longitudinal sectional view showing a state of the as-extruded superconducting wire.

Referring to FIG. 22, the copper cover portion 19 of the as-extruded superconducting wire includes a portion 29 which is thinned due to the rearward feeding of the copper, and the copper bank 25. Therefore, such a superconducting wire has dispersion in a sectional area ratio between a first material part and a second material part, and as a result, in copper ratio along its longitudinal direction.

The copper ratio is strictly defined in relation to application of the superconducting wire, as hereinabove described, so that a current flows into the copper serving as a stabilizing material when a superconducting state of the product is broken. If the copper ratio is dispersed along the longitudinal direction in the target wire diameter, therefore, the following problem arises:

When the copper ratio is low, the current cannot bypass toward the copper upon breakage of the superconducting state since the area of the copper is too small, and this may lead to a significant trouble such as burning of the wire. If the copper ratio is low, further, the area of the superconducting part is increased. Namely, a target draft cannot be sufficiently attained as to each superconducting filament, and hence a required critical current value may not be satisfied. When the copper ratio is high, on the other hand, the area of the important superconducting part is reduced and hence the superconducting part itself may not satisfy a required critical current value.

SUMMARY OF THE INVENTION

An object of the present invention is to solve the aforementioned problems and provide a method of measuring a sectional area ratio between a first material part and a second material part of a metal-covered electric wire having the core part including the first material and a metal covering layer formed of the second material covering the core part.

Another object of the present invention is to provide a method of adjusting a sectional area ratio between a first material part and a second material part of a metal-covered electric wire after wire drawing.

Still another object of the present invention is to provide a method of uniformalizing a sectional area ratio between a first material part and a second material part of a metal-covered electric wire along its longitudinal direction.

A further object of the present invention is to provide a method of efficiently cleaning a surface of an electric wire having a metal surface in a short time.

A further object of the present invention is to provide a method of manufacturing a superconducting wire utilizing electropolishing.

A further object of the present invention is to provide an apparatus for measuring in a nondestructive manner, a sectional area ratio between a first material part and a second material part of a metal-covered electric wire.

A further object of the present invention is to provide an apparatus for electropolishing an electric wire.

According to an aspect of the present invention, provided is a method of measuring a sectional area ratio between a first material part and a second material part of a metal-covered electric wire having a core part including the first material and a metal covering layer formed of the second material covering the core part. This method comprises a step of previously storing electric resistance values of the first and second materials respectively, a step of measuring electric resistance of the metal-covered electric wire over a prescribed length region, a step of calculating a sectional area ratio between the first material part and the second material part in the prescribed length region on the basis of the previously stored electric resistance values of the first and second materials and the actually measured electric resistance of the metal-covered electric wire, and a step of moving the metal-covered electric wire continuously along its longitudinal direction, to measure distribution of the sectional area ratio in the longitudinal direction of the metal-covered electric wire.

Preferably, the step of measuring electric resistance of the metal-covered electric wire includes a step of feeding a current to the prescribed length region of the metal-covered electric wire through a pair of first electrodes, a step of measuring a voltage developed in the prescribed length region of the metal-covered electric wire through a pair of second electrodes which are placed inside the pair of first electrodes, and a step of calculating the electric resistance of the prescribed length region in the metal-covered electric wire on the basis of the as-applied current value and the as-measured voltage value.

Preferably, the first material is a superconducting material, and the second material is copper or a copper alloy. In that case, the core part of a wire having a single core consists only of a superconducting material, while the core part of a wire having multiple cores includes a conductive material and a stabilizing material formed of copper or copper alloy.

According to another aspect of the present invention, provided is a method of adjusting a sectional area ratio between a first material part and a second material part of a metal-covered electric wire having the core part including the first material and a metal covering layer formed of the second material covering the core part, by dissolving a surface layer part of the covering layer by electropolishing.

Preferably, an electrolyte is electrolyzed through an anode of the electric wire dipped in an electrolytic bath and a cathode of a metal placed in the electrolytic bath in the electropolishing, thereby dissolving a surface layer part of the electric wire serving as an anode.

Preferably, the electrolytic process includes a step of continuously moving the electric wire along its longitudinal direction for continuously passing the same through the electrolytic bath, and a step of electrolyzing the electrolyte through an anode of the electric wire dipped in the electrolytic bath and a cathode of the metal placed in the electrolytic bath for dissolving the surface layer part of the electric wire serving as an anode.

Preferably, the second material is a metal selected from a group of zinc, aluminum, gold, silver, chromium, tin, tungsten, iron, copper and nickel, or an alloy thereof.

Preferably, the first material is a superconducting material, and the second material is copper or a copper alloy.

According to still another aspect of the present invention, provided is a method of uniformalizing a sectional area ratio between a first material part and a second material part of a metal-covered electric wire by dissolving a surface layer part of the covering layer of the metal-covered electric wire having the core part including the first material and the metal covering layer formed of the second material covering the first material part by electropolishing for uniformalizing the sectional area ratio between the first material part and the second material part along the longitudinal direction.

Preferably, an electrolyte is electrolyzed through an anode of the electric wire dipped in an electrolytic bath and a cathode of a metal placed in the electrolytic bath in the electropolishing, thereby dissolving a surface layer part of the electric wire serving as an anode.

Preferably, the electropolishing includes a step of continuously moving the electric wire along its longitudinal direction for continuously passing the same through the electrolytic bath, and a step of electrolyzing the electrolyte through an anode of the electric wire dipped in the electrolytic bath and a cathode of the metal placed in the electrolytic bath for dissolving the surface layer part of the electric wire serving as an anode.

Preferably, the value of a current which is applied to the electrolyte is varied to control the amount of dissolution of the surface layer part of the electric wire.

Preferably, the second material is a metal selected from a group of zinc, aluminum, gold, silver, chromium, tin, tungsten, iron, copper and nickel, or an alloy thereof.

Preferably, the first material is a superconducting material, and the second material is copper or a copper alloy.

According to a further aspect of the present invention, provided is a method of cleaning an electric wire by removing a surface layer part of the electric wire having a metal surface by electropolishing.

Preferably, an electrolyte is electrolyzed through an anode of the electric wire dipped in an electrolytic bath and a cathode of a metal placed in the electrolytic bath in the electropolishing, thereby dissolving a surface layer part of the electric wire serving as an anode.

Preferably, the electropolishing includes a step of continuously moving the electric wire along its longitudinal direction for continuously passing the same through the electrolytic bath, and a step of electrolyzing the electrolyte through an anode of the electric wire dipped in the electrolytic bath and a cathode of the metal placed in the electrolytic bath for dissolving the surface layer part of the electric wire serving as an anode.

Preferably, the metal is a metal selected from a group of zinc, aluminum, gold, silver, chromium, tin, tungsten, iron, copper and nickel, or an alloy thereof.

Preferably, the electric wire includes a core part including a superconducting material, and a covering layer formed of copper or a copper alloy covering the core part.

According to a further aspect of the present invention, a method of manufacturing a metal-covered electric wire is provided. This method comprises a step of charging a metal pipe formed of a second material with a material for defining a core including a first material for preparing a billet, a step of extruding the as-prepared billet, a step of wire-drawing the as-extruded body for preparing a metal-covered electric wire, and a step of removing a surface layer part of the electric wire by electropolishing.

Preferably, an electrolyte is electrolyzed through an anode of the electric wire dipped in an electrolytic bath and a cathode of a metal placed in the electrolytic bath in the electropolishing, thereby dissolving a surface layer part of the electric wire serving as an anode.

Preferably, the electropolishing includes a step of continuously moving the electric wire along its longitudinal direction for continuously passing the same through the electrolytic bath, and a step of electrolyzing the electrolyte through an anode of the electric wire dipped in the electrolytic bath and a cathode of the metal placed in the electrolytic bath for dissolving the surface layer part of the electric wire serving as an anode.

Preferably, the method further comprises a step of measuring a distribution state of the sectional area ratio between the first material part and the second material part along the longitudinal direction of the electric wire.

Preferably, the amount of removal of the surface layer part is adjusted in response to the as-measured distribution state of the sectional area ratio to uniformalize the sectional area ratio along the longitudinal direction in the step of removing a surface layer part of the electric wire by electropolishing.

Preferably, the amount of removal of the surface layer part is adjusted by changing the value of a current which is applied to the electrolyte.

Preferably, the amount of removal of the surface layer part is adjusted by varying the speed for moving the electric wire.

Preferably, the method further comprises a step of further wire-drawing the electropolished electric wire for uniformalizing the wire diameter of the electric wire along the longitudinal direction.

Preferably, the surface layer part is removed by electropolishing until the sectional area ratio between the first material part and the second material part of the electric wire reaches a prescribed value.

Preferably, the surface layer is removed by electropolishing to sufficiently remove defects on the surface of the electric wire and foreign matters adhering thereto.

Preferably, the electric wire includes a core part including a superconducting material and a covering layer formed of copper or a copper alloy covering the core part.

Preferably, a surface current density of the electric wire is set at 1 to 200 A/dm$^2$ in electropolishing.

According to a further aspect of the present invention, provided is an apparatus for measuring, in a nondestructive manner, a sectional area ratio between a first material part and a second material part of a metal-covered electric wire having a core part including the first material and a metal covering layer formed of the second material covering the core part. This apparatus comprises means for previously storing electric resistance values of the first and second materials respectively, a pair of first electrodes for feeding a current to a prescribed length region of the metal-covered electric wire, a pair of second electrodes which are placed inside the pair of first electrodes for measuring a voltage developed in the prescribed length region of the metal-covered electric wire, means for calculating electric resistance of the metal-covered electric wire in the prescribed length region on the basis of the as-applied current value and the as-measured voltage value, and means for calculating a sectional area ratio between the first material part and the second material part in the prescribed length region on the basis of the previously stored electric resistance values of the first and second materials and the actually measured electric resistance of the metal-covered electric wire.

Preferably, the apparatus further comprises means for continuously moving the metal-covered electric wire along its longitudinal direction, for measuring distribution of the sectional area ratio of the metal-covered electric wire along the longitudinal direction.

According to a further aspect of the present invention, an apparatus for electropolishing an electric wire is provided. This apparatus comprises an electrolytic bath containing an electrolyte, means for continuously moving an electric wire having a metal surface along its longitudinal direction for continuously passing the same through the electrolytic bath, means for anodizing the electric wire, a metal member arranged in the electrolytic bath for serving as a cathode, and means for causing potential difference between the electric wire and the metal member for dissolving a surface layer part of the electric wire by electropolishing.

Preferably, the electrolytic bath comprises rollers for winding the electric wire which is passed through the electrolytic bath.

Preferably, the means for moving the electric wire includes means which can change its speed.

Preferably, the apparatus further includes means which can change the amount of a current which is applied to the electrolyte.

According to a further aspect of the present invention, provided is an apparatus for uniformalizing a sectional area ratio between a first material part and a second material part of a metal-covered electric wire having the core part including the first material and a metal covering layer formed of the second material covering the core part along its longitudinal direction. This apparatus comprises means for previously storing electric resistance values of the first and second materials respectively, a pair of first electrodes for feeding a current to a prescribed length region of the metal-covered electric wire, a pair of second electrodes which are placed inside the pair of first electrodes for measuring a voltage developed in the prescribed length region of the metal-covered electric wire, means for calculating electric resistance of the metal-covered electric wire in the prescribed length region on the basis of the as-applied current value and the as-measured voltage value, means for calculating a sectional area ratio between the first material part and the second material part in the prescribed length region on the basis of the previously stored electric resistance values of the first and second materials and the actually measured electric resistance of the metal-covered electric wire, an electrolytic bath containing an electrolyte, means for anodizing the electric wire, a metal member arranged in the electrolytic bath for serving as a cathode, means for causing potential difference between the electric wire and the metal wire for dissolving a surface layer part of the electric wire by electropolishing, means for continuously moving the electric wire along the longitudinal direction for continuously passing the same through the electrolytic bath in continuation to the measurement of the sectional area ratio, and means for controlling the amount of dissolution of the surface layer part of the electric wire in response to the result of measurement of the sectional area ratio.

According to one aspect of the present invention, it is possible to measure the sectional area ratio between the first material part and the second material part of the metal-covered electric wire in a nondestructive manner. Thus, the sectional area ratio can be measured in any position, while distribution along the overall length of the electric wire can also be measured by continuous measurement.

When the present invention is applied to quality control in manufacturing of a superconducting wire or the like, for example, a defective part can be ascertained to improve the yield in manufacturing by removing the defective part with no loss.

Further, the present invention is applicable not only to a final product but to a metal-covered electric wire having an intermediate wire diameter in manufacturing steps. Therefore, the present invention is effectively applicable also for manufacturing of an electric wire having a uniform sectional area ratio between a first material part and a second material part.

According to the present invention, the sectional area ratio between the first material part and the second material part is calculated along the following equation (1), from the previously stored electric resistance values of the first and second materials and the actually measured electric resistance of the metal-covered electric wire:

$$\text{Sectional Area Ratio} = \{(R \cdot S/\rho sc) - L\} / \{L - (R \cdot S/\rho cu)\} \quad (1)$$

where $R = V/\{I \cdot (1+\alpha)(T-20)\}$, and V represents the as-measured voltage, I represents an energization current, $\alpha$ represents a temperature coefficient of resistance ($1/°C$) at a constant mass, at a temperature of 20° C. as a reference, T represents the temperature of the wire, S denotes the sectional area of the wire, L denotes a tap-to-tap length, $\rho sc$ denotes resistivity of the first material, and $\rho cu$ denotes resistivity of the second material.

This equation (1) is now described.

It is assumed that R represents resistance of the metal-covered electric wire, Rcu represents that of the second material, and Rsc represents that of the first material.

In the case of a composite, the overall resistance is conceivably formed by parallel connection of respective resistance values. Hence, the following equation |1| holds:

$$1/R = 1/Rcu + 1/Rsc \therefore R = (Rcu \cdot Rsc)/(Rcu + Rsc) \qquad |1|$$

Assuming that S represents the sectional area of the metal-covered electric wire, Scu represents that of the second material part, Ssc represents that of the first material part and X represents the sectional area ratio of the second material part to the first material part, the following equations |2| and |3| hold:

$$X = Scu/Ssc \qquad |2|$$

$$S = Ssc + Scu \qquad |3|$$

On the other hand, the resistance values of the second materials and the first materials can be expressed as follows, assuming that ρcu and ρsc represent respective specific resistance values thereof:

$$Rcu = \rho cu \cdot (L/Scu) \qquad |4|$$

$$Rsc = \rho sc \cdot (L/Ssc) \qquad |5|$$

where L represents a tap-to-tap length, which is in common for the second material part and the first material part. Hence, the following equations |6| and |7| are obtained from the equations |2|, |3|, |4| and |5|:

$$Rcu = \{\rho cu \cdot L(X+1)\}/SX \qquad |6|$$

$$Rsc = \{\rho sc \cdot L(X+1)\}/S \qquad |7|$$

Substitution of the equations |6| and |7| in the equation |1| gives the following equation |8|:

$$R = \{L(X+1) \cdot \rho cu \cdot \rho sc\}/\{S(\rho cu + X \cdot \rho sc)\} \qquad |8|$$

From this equation |8|, the aforementioned equation (1) is obtained as follows:

$$X = \{R \cdot S/\rho sc\} - L\}/\{L - (R \cdot S/\rho cu)\}$$

According to another aspect of the present invention, it is possible to adjust the sectional area ratio between the first material part and the second material part by dissolving the surface layer part of the covering layer of the metal-covered electric wire by electropolishing. Namely, a target amount of dissolution can be easily and uniformly obtained by electropolishing, whereby it is possible to work a metal-covered electric wire having a certain sectional area ratio into an electric wire having a lower sectional area ratio by dissolving its surface layer part. Thus, the sectional area ratio can be changed in manufacturing steps, whereby electric wire products for various uses can be prepared from a single starting material. Thus, the manufacturing steps are simplified.

According to still another aspect of the present invention, it is possible to uniformalize the sectional area ratio between the first material part and the second material part along the longitudinal direction by dissolving the surface layer part of the covering layer of the metal-covered electric wire by electropolishing. Namely, it is possible to easily and uniformly obtain a target amount of dissolution by electropolishing, whereby the sectional area ratio can be uniformalizing by previously measuring the sectional area ratio of the metal-covered electric wire and calculating an amount of dissolution for attaining a specific sectional area ratio and dissolving the surface layer part of the covering layer in electropolishing so that a part having a high sectional area is dissolved in a large amount and a part having a low sectional area is dissolved in a small amount in response to the measured value and the calculated value. Consequently, the yield in manufacturing of the metal-covered electric wire is improved and reduction in cost can be expected.

The amount of dissolution can be adjusted by varying a current which is applied to the electrolyte in electropolishing. The amount of dissolution is increased when the current is increased, while the same is reduced when the current is reduced.

The amount of dissolution can also be adjusted by changing the speed for moving the superconducting wire. Namely, the amount of dissolution of the metal covering layer is reduced when the speed for moving the metal-covered electric wire is increased, since the time for passing the wire through the electrolyte is reduced. When the speed for moving the electric wire is reduced, on the other hand, the amount of dissolution of the covering layer is increased since the time for passing the electric wire through the electrolyte is increased.

According to the further aspect of the present invention, it is possible to clean the surface of the electric wire by removing the surface layer part of the electric wire having a metal surface. Namely, it is possible to dissolve a larger amount of skin by electropolishing as compared with conventional acid cleaning or the like, as well as to easily and uniformly attain a target amount of dissolution. Namely, it is possible to remove foreign matters adhering to the surface and smoothly finish the surface by efficiently dissolving a larger amount of skin in a shorter time than the prior art. Consequently, it is also possible to prevent wire breaking, which has been generally caused by foreign matters.

According to the further aspect of the present invention, electropolishing is employed in the method of manufacturing a metal-covered electric wire. It is possible to adjust and uniformalize the sectional area ratio, or clean the surface.

The wire diameter of a metal-covered electric wire which is uniformalized in sectional area ratio by electropolishing is irregularized along the longitudinal direction. Therefore, this electric wire having an irregular wire diameter is again subjected to die-drawing, so that its wire diameter can be uniformalized.

When the electric wire has a surface current density of 1 to 200 A/dm$^2$ in electropolishing, the metal covering layer can be dissolved with no surface irregularity and a number of bubbly hollow portions in the electric wire in electropolishing.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
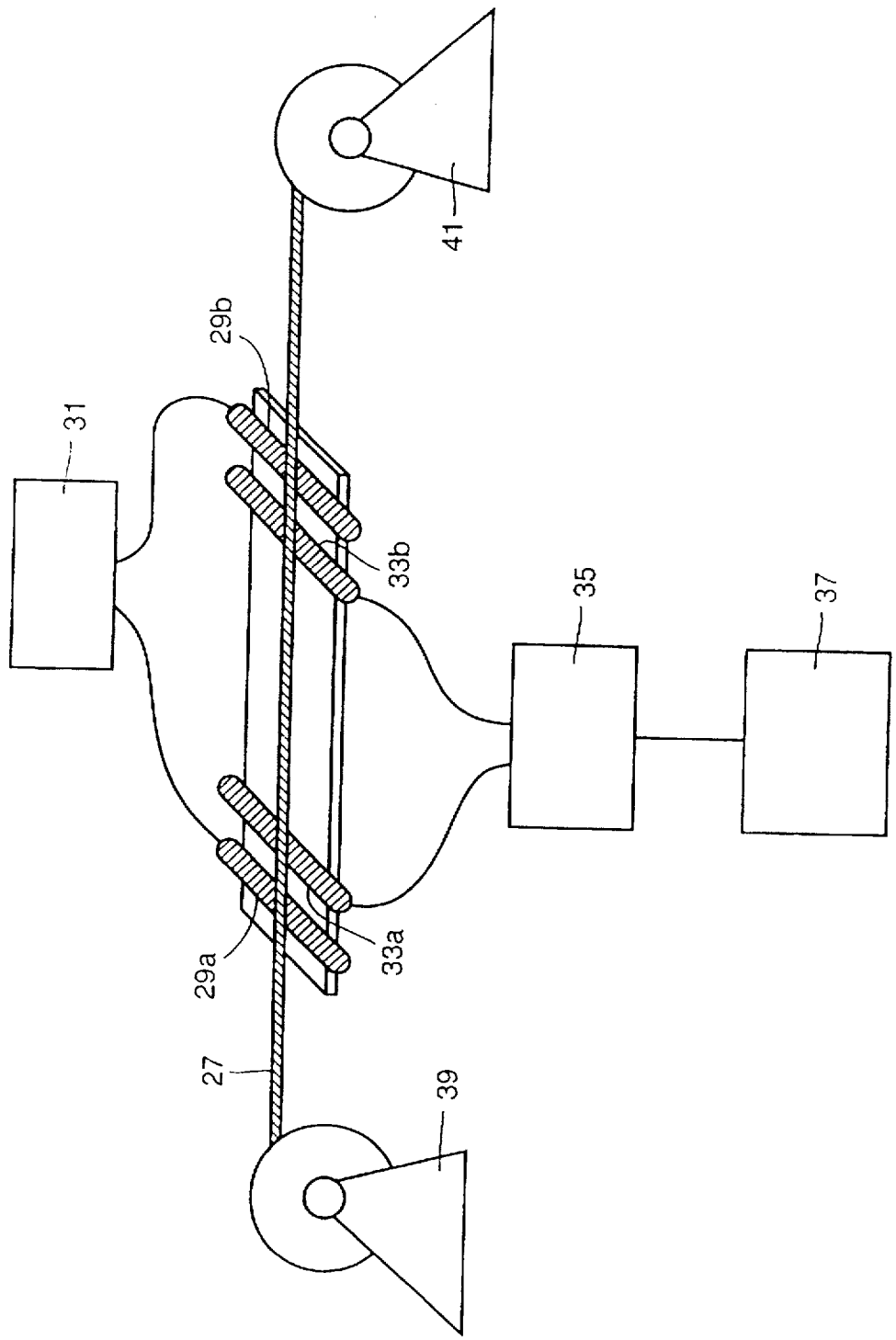
FIG. 1 schematically illustrates an exemplary apparatus for measuring an overall length sectional area ratio of a metal-covered electric wire according to the present invention.

FIG. 1 schematically illustrates an exemplary apparatus for measuring a sectional area ratio between a first material part and a second material part of a metal-covered electric wire in a nondestructive manner according to the present invention.

Referring to FIG. 1, this measuring apparatus comprises a constant current source 31 for applying a constant current to an electric wire 27 through a pair of first electrodes 29a and 29b, and a voltmeter 35 for measuring a voltage developed across a pair of second electrodes 33a and 33b. The pair of second electrodes 33a and 33b are provided inside the pair of first electrodes 29a and 29b. The voltmeter 35 is connected with a computer 37 for converting the as-measured voltage to an electric resistance value and continuously calculating the sectional area ratio. This measuring apparatus further comprises supply means 39 and take-up means 41, for continuously measuring the voltage of the electric wire 27.

The measuring apparatus having the aforementioned structure is adapted to measure an overall length copper ratio of a Cu composite superconducting wire, for example, in the following manner:

First, electric resistance values of a stabilizing material part of Cu or a Cu alloy and a superconducting material part of the Cu composite superconducting wire 27 are previously measured respectively, and the as-obtained data are inputted in the computer 37.

Then, the Cu composite superconducting wire 27 is continuously delivered from the supply means 39 and wound on the take-up means 41, so that electric resistance of the Cu composite superconducting wire 27 is continuously measured along its longitudinal direction. The electric resistance of the Cu composite superconducting wire 27 is measured by applying a constant current from the constant current source 31 through the pair of first electrodes 29a and 29b, measuring a voltage which is developed across the pair of second electrodes 33a and 33b by the voltmeter 35, and further converting the voltage to an electric resistance value by the computer 37.

Further, the computer 37 continuously calculates a Cu/SC sectional area ratio along the above equation (1), in response to the previously inputted electric resistance values of the stabilizing material part of Cu or a Cu alloy and the superconducting material part and the electric resistance of the Cu composite superconducting wire 27 continuously measured in the aforementioned manner.

Figure 2:
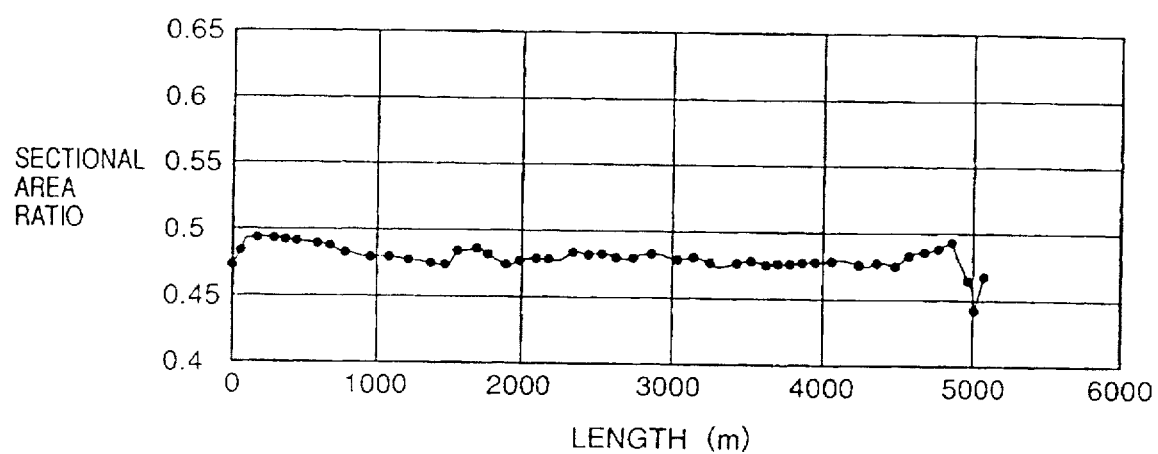
FIG. 2 illustrates the result of measurement of an overall copper ratio of a Cu-covered superconducting wire measured by the present invention.

An overall length copper ratio of a Cu composite superconducting wire having an outer diameter of 3 mm was actually measured over a length of about 5000 m by the aforementioned measuring method. The measurement was carried out along the overall length at intervals of 100 m. FIG. 2 shows the result. Referring to FIG. 2, the axis of abscissas shows the length (m) of the wire, and the axis of ordinates shows the Cu/SC sectional area ratio.

It is clearly understood from FIG. 2 that distribution of a Cu/SC sectional area ratio of a Cu composite superconducting wire can be thus measured along the overall length in a nondestructive manner.

When the present invention is applied to quality control or the like in manufacturing of a superconducting wire, for example, defective parts can be ascertained and hence it is possible to improve the yield in manufacturing by removing the defective parts with no loss. Further, the present invention is applicable not only to a final product but to a metal-covered electric wire having an intermediate wire diameter during manufacturing steps. Therefore, the present invention is also effectively applicable to manufacturing of a Cu composite superconducting wire having a uniform Cu/SC sectional area ratio.

When electrodes for a four-probe method are set in a line having mechanisms of supply means and take-up means and a certain constant current is fed from the electrodes for the four-probe method while driving a wire thereby continuously measuring its voltage as in the aforementioned embodiment, the measuring frequency may be analogously incorporated through the electrodes in the form of rollers, while measurement may alternatively be carried out every constant position.

This measuring apparatus is widely applicable not only to a Cu-covered superconducting wire but to nondestructive measurement of a sectional area ratio between a first material part and a second material part of a metal-covered electric wire having the core part including the first material and the metal covering layer formed of the second material covering the core part.

Figure 3:
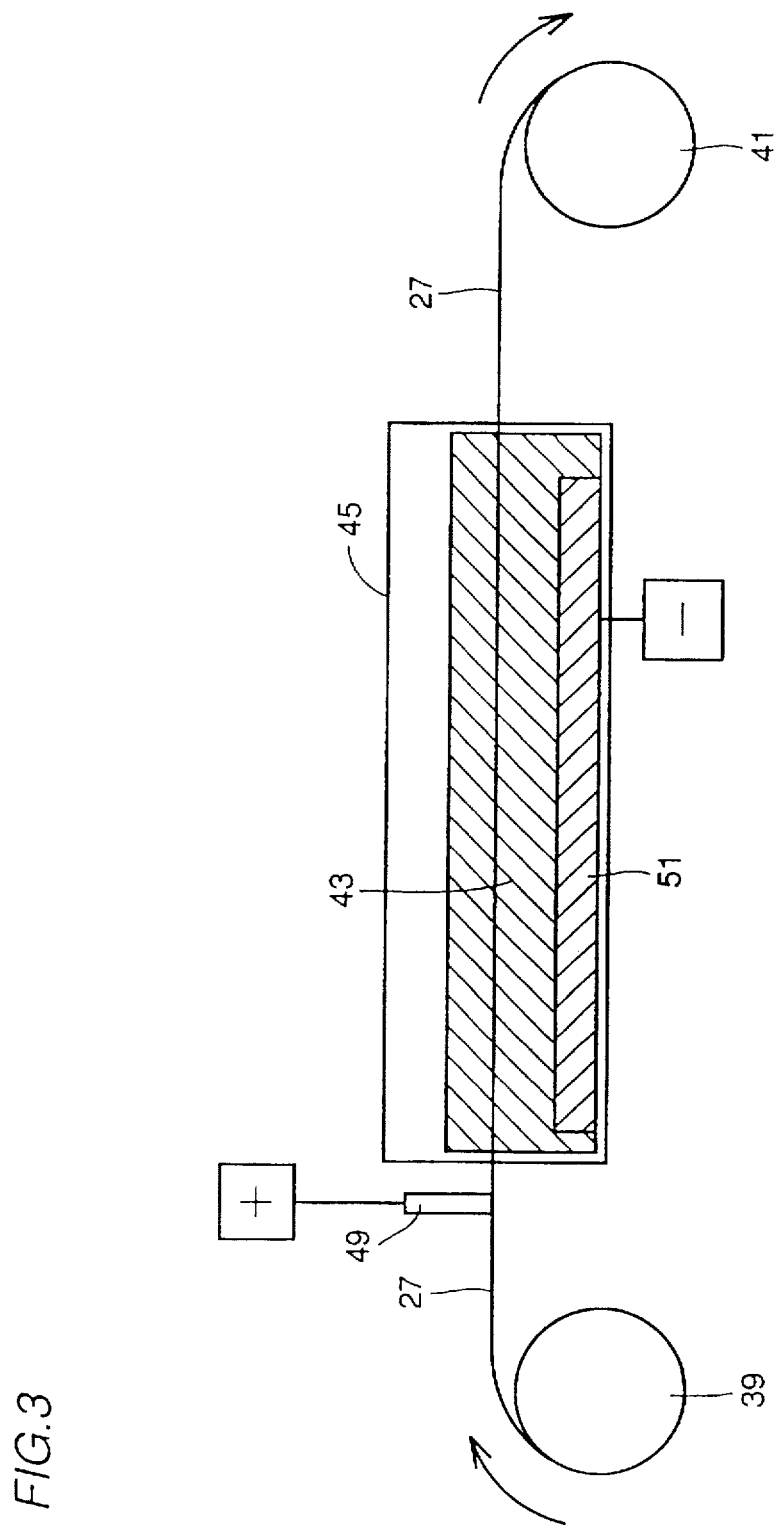
FIG. 3 schematically illustrates an exemplary apparatus for electropolishing a metal-covered electric wire according to the present invention.

FIG. 3 schematically illustrates an exemplary apparatus for electropolishing a metal-covered electric wire according to the present invention.

Referring to FIG. 3, this electropolishing apparatus comprises an electrolytic bath 45 containing an electrolyte 43, a feed part 49 for anodizing an electric wire 27, and a metal member 51 which is arranged in the electrolytic bath 45 for serving as a cathode, and is so formed that potential difference is caused between the electric wire 27 and the metal member 51. This apparatus further comprises supply means 39 and take-up means 41 for continuously moving the electric wire 27 along its longitudinal direction for continuously passing the same through the electrolytic path 45.

In the electropolishing apparatus having the aforementioned structure, the electric wire 27 which is wound on the supply means 39 is passed through the electrolyte 43 containing the metal member 51 serving as a cathode while being fed with electricity to serve as an anode. Then, the skin of the electric wire 27 is dissolved by an electrolytic process. The electric wire 27 thus dissolved/polished is wound on the take-up means 41. These steps are continuously carried out.

In this case, the amount of dissolution of the metal covering layer can be controlled through the value of the current which is applied to the electrolyte and the speed for moving the electric wire.

Figure 4:
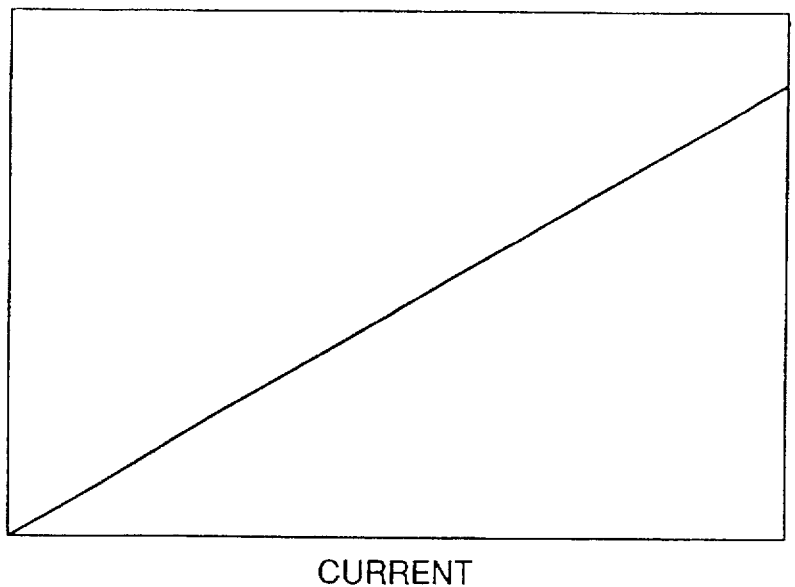
FIG. 4 illustrates relation between a current and an amount of dissolution in electropolishing.

FIG. 4 shows relation between the value of a current which is applied to an electrolyte and an amount of dissolution of a metal covering layer in electropolishing. It is understood from FIG. 4 that the amount of dissolution is increased as the current value is increased.

Figure 5:
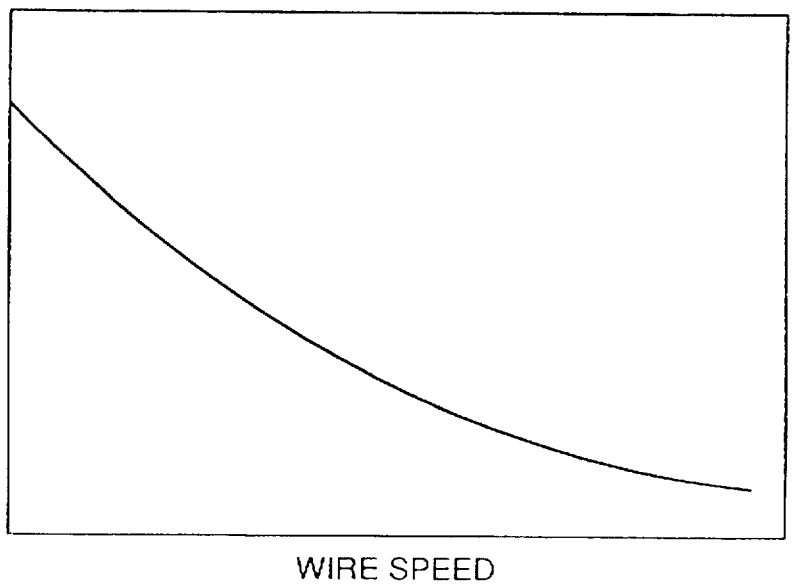
FIG. 5 illustrates relation between a wire speed and an amount of dissolution in electropolishing.

FIG. 5 illustrates relation between the speed for moving an electric wire and the amount of dissolution of a metal covering layer in electropolishing. It is understood from FIG. 5 that the amount of dissolution is reduced as the speed for moving the electric wire is increased.

This electropolishing apparatus was employed to actually adjust copper ratios of Cu-covered superconducting wires. Concrete examples are now described.

(EXAMPLE 1)

The electropolishing apparatus shown in FIG. 3 was employed to electropolish 1000 m of a superconducting single-core wire having a copper ratio of 1.00 and a wire diameter of 3 mm in a phosphoric acid bath in a stage of manufacturing a superconducting wire so that an amount of dissolution on one side of its skin was 50 µm, to attain a target copper ratio of 0.87.

(COMPARATIVE EXAMPLE 1)

In a stage of manufacturing a superconducting wire, 1000 m of a superconducting single-core wire having a copper ratio of 1.00 and a wire diameter of 3 mm was dissolved with dilute sulfuric acid so that an amount of dissolution on one side of its skin was 50 µm, to attain a target copper ratio of 0.87.

Consequently, it was possible to finish the superconducting wire with the target copper ratio of 0.87 along the overall length in the method of Example 1 employing electropolising, through a dipping time of 0.3 hours. In comparative example 1, however, it was impossible to finish the wire at the same copper ratio along the overall length since dissolving power of the acid was reduced with dissolution, although the wire was dipped for 3 hours. In order to attain the same amount of dissolution by acid dissolution, on the other hand, an amount of tens of times was required as compared with the acid employed in the electropolishing.

(EXAMPLE 2)

In order to adjust the copper ratio of the superconducting wire in Example 1 by electropolishing, the copper skin on a surface of a superconducting multicore wire was dissolved with a surface current density of 100 A/dm$^2$.

(EXAMPLE 3)

In order to adjust the copper ratio of the superconducting wire in Example 1 by electropolishing, the copper skin of a surface of a superconducting multicore wire was dissolved with a surface current density of 300 A/dm$^2$.

The as-manufactured superconducting wires of Examples 2 and 3 were compared with each other. As the result, the superconducting wire of Example 2 had an extremely smooth surface after copper dissolution. In the superconducting wire of Example 3, on the other hand, large amounts of molten metal creases and blowholes were caused since the surface current density was too high in electropolishing.

(EXAMPLE 4)

In a stage of manufacturing a superconducting wire, 1000 m of a superconducting single-core wire having a copper ratio of 1.00 and a wire diameter of 3 mm was electropolished in a phosphoric acid bath through the electropolishing apparatus shown in FIG. 3 so that an amount of dissolution on one side of its skin was 50 µm, to attain a target copper ratio of 0.87. At this time, the distance between the superconducting wire 27 and the metal member 51 in the phosphoric acid bath 43 was 5 cm.

(EXAMPLE 5)

In a stage of manufacturing a superconducting wire, 60 m of a superconducting single-core wire having a copper ratio of 1.00 and a wire diameter of 12 mm was electropolished in a phosphoric acid bath through the electropolishing apparatus shown in FIG. 3 so that an amount of dissolution on one side of its skin was 200 µm, to attain a target copper ratio of 0.87. At this time, the distance between the superconducting wire 27 and the metal member 51 in the phosphoric acid bath 43 was 5 cm.

The as-manufactured superconducting wires of Examples 4 and 5 were compared with each other. As the result, the superconducting wire of Example 4 was uniformly dissolved along its circumferential direction, while the superconducting wire of Example 5 was ununiformly dissolved along its circumferential direction since it was difficult to maintain a distance between the overall circumference from a minus electrode at a constant level.

Thus, it is understood that the copper ratio can be adjusted in a short time during manufacturing steps by electropolishing. In the electropolishing, the superconducting wire preferably has a surface current density of 1 to 200 A/dm$^2$.

A method of manufacturing a superconducting wire includes tens of steps between states of a raw material and a product, and hence it is assumed in a considerable frequency that difference is caused between billets due to working. This also applies to the copper ratio, such that dispersion between lots is generally extremely problematic in addition to dispersion in a lot (along the longitudinal direction of a single wire). According to the present invention, it is possible to correct dispersion in copper ratio after wire drawing.

This electropolishing apparatus is widely applicable not only to a Cu-covered superconducting wire but to adjustment of a sectional area ratio between a core part and a metal covering layer in a metal-covered electric wire having the core part and the metal covering layer covering the core part.

In this case, the covering layer to which the present invention is applicable is conceivably prepared from a material having excellent electric conductivity such as zinc, aluminum, gold, silver, chromium, tin, tungsten, iron, copper or nickel. This is because a certain degree of surface current density is required for electropolishing, and a material having inferior electric conductivity may lead to heat generation at this time.

The electrolyte, which is varied with compatibility with the metal to be dissolved, may conceivably be prepared from acid such as perchloric acid, phosphoric acid, sulfuric acid, chromic acid, nitric acid, sodium hydroxide, potassium hydroxide, cyan or the like. Acid such as phosphoric acid or sulfuric acid is preferable for dissolving copper, for example.

The electropolishing step may be carried out in any stage during the steps of manufacturing a metal-covered electric wire.

Surfaces of Cu-covered superconducting wires were cleaned through the electropolishing apparatus. Concrete examples are now described.

(EXAMPLE 6)

In order to remove foreign matters in a stage of manufacturing a superconducting wire, 5000 m of a superconducting multicore wire having a diameter of 3 mm was electropolished in a phosphoric acid bath through the electropolishing apparatus shown in FIG. 3, so that an amount of dissolution on one side of its skin was 30 μm. Thereafter the wire was drawn to 0.8 mm.

(COMPARATIVE EXAMPLE 2)

In order to remove foreign matters in a stage of manufacturing a superconducting wire, 5000 m of a superconducting multicore wire having a wire diameter of 3 mm was dissolved with dilute sulfuric acid so that an amount of dissolution on one side of its skin was 30 μm. Thereafter the wire was drawn to 0.8 mm.

As the result, the superconducting wire of Example 6 was broken once by foreign matters, while the superconducting wire of comparative example 2 was broken 20 times by foreign matters. This is conceivably because the foreign matters were further completely removed by the electropolishing, which is capable of attaining dissolution in a larger amount than acid dissolution.

This electropolishing apparatus is widely applicable not only to a Cu-covered superconducting wire but to cleaning of a surface of an electric wire having a metal surface.

In this case, the metal forming the surface is conceivably prepared from a material having excellent electric conductivity such as zinc, aluminum, gold, silver, chromium, tin, tungsten, iron, copper or nickel. This is because a certain degree of surface current density is required for electropolishing, and a material having inferior electric conductivity may lead to heat generation at this time.

The electrolyte, which is varied with compatibility with the metal to be dissolved, may conceivably be prepared from acid such as perchloric acid, phosphoric acid, sulfuric acid, chromic acid, nitric acid, sodium hydroxide, potassium hydroxide, cyan or the like. Acid such as phosphoric acid or sulfuric acid is preferable for dissolving copper, for example.

Further, the electropolishing step may be carried out in any stage in the steps of manufacturing a metal-covered electric wire, while it is conceivably effective to clean the wire before there arises a possibility of wire breaking when the cleaning is carried out in order to suppress wire breaking in wire drawing.

In the following, a method of making uniform the cross sectional area of the metal-covered electric wire employing electropolishing will be described in greater detail.

Figure 6:
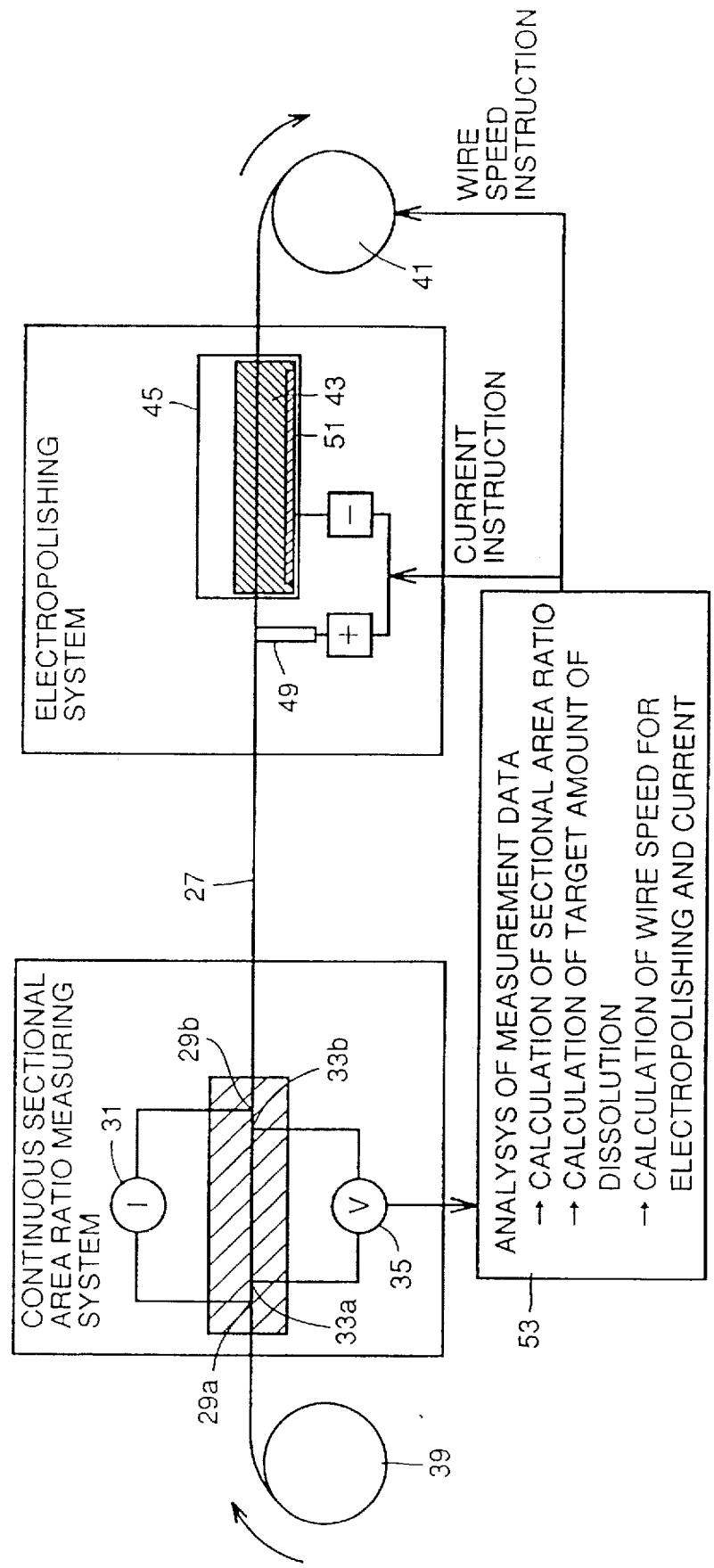
FIG. 6 schematically illustrates an exemplary apparatus incorporating measurement of sectional area ratio and electropolishing of a metal-covered electric wire according to the present invention.

FIG. 6 schematically illustrates another exemplary electropolishing apparatus for uniformalizing a sectional area ratio between a first material part and a second material part of a metal-covered electric wire along its longitudinal direction according to the present invention.

Referring to FIG. 6, this electropolishing apparatus is formed by combining the measuring apparatus shown in FIG. 1 with the electropolishing apparatus shown in FIG. 3.

This apparatus comprises a constant current source 31 for applying a constant current to an electric wire 27 through a pair of first electrodes 29a and 29b, and a voltmeter 35 for measuring a voltage developed across a pair of second electrodes 33a and 33b, as a continuous sectional area ratio measuring system. The pair of second electrodes 33a and 33b are provided inside the pair of first electrodes 29a and 29b. This apparatus further comprises an electrolytic bath 45 containing an electropolishing solution 43, a feed part 49 for anodizing the electric wire 27, and a metal member 51 which is arranged in the electrolytic bath 45 for serving as a cathode as an electropolishing system, and is so formed that potential difference is caused between the electric wire 27 and the metal member 51. The apparatus further comprises supply means 39 and take-up means 41 for continuously measuring the voltage of the electric wire 27 and continuously moving the electric wire 27 along its longitudinal direction to continuously pass the same through the electrolytic bath 45.

In this apparatus, a computer 53 which is connected with the voltmeter 35 converts the as-measured voltage to an electric resistance value to continuously calculate the sectional area ratio, while calculating an amount of dissolution for attaining a target sectional area ratio, calculating a wire speed for moving the electric wire 27 and an amount of the current which is applied to the electrolyte and indicating the as-calculated speed and current values.

The amount of dissolution for attaining the target sectional area ratio can be obtained through the following equation (2), under the condition that the sectional area ratio in advance of dissolution is larger than the target sectional area ratio:

$$(D_2/D_1)^2 = \{(1 \times C_2)/(1+C_1)\} \tag{2}$$

where $D_1$ represents the wire diameter in advance of the electrolytic process, $C_1$ represents the sectional area ratio in advance of the electrolytic process, $D_2$ represents the target wire diameter, and $C_2$ represents the target sectional area ratio.

As to adjustment of the amount of dissolution with time, it is possible to easily decide manufacturing conditions by previously obtaining relation between the current, the wire speed and the amount of polishing by an experiment and recognizing the amount to be dissolved. Particularly when the apparatus is employed for adjusting the sectional area ratio along the longitudinal direction, relation between the position of the wire, the current and the wire speed may be previously calculated from the target amount of dissolution, to pattern-control the same in the line. Namely, it is possible to time-control the amount of dissolution by inputting the position of the wire which is passed through the line from a meter.

Electropolishing conditions are set from the result of measurement of the sectional area ratio in the following manner, for example:

First, a constant current is fed at a constant space by a four-probe method to measure "wire position—voltage characteristic" data and thereafter the value is calculated by a computer to obtain "wire position—electric resistance characteristic"→"wire position— sectional area ratio characteristic"→"wire position—required amount of dissolution"→"wire position—current/wire speed", the pattern is written in a computer controlling the electropolishing apparatus, and when the line is driven the amount of the current and the wire speed are automatically controlled to obtain the target amount of dissolution.

In order to keep the wire dipped in the electrolyte for a longer period of time, the electrolytic bath must be made long. However, it becomes possible to dip a wire longer than the length of the electrolytic bath in the electrolyte by coiling or winding the wire.

Figure 7:
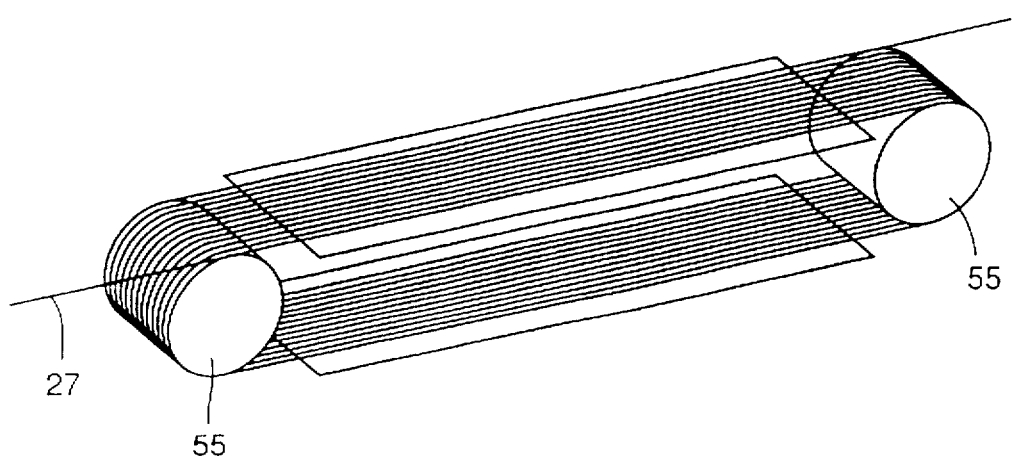
FIG. 7 illustrates a state of winding an electric wire.

FIG. 7 is a plan view showing a state of winding an electric wire 27 in an electrolytic bath.

Referring to FIG. 7, the electric wire 27 is wound by a plurality of turns through sieve rollers 55, so that it is possible to dip the electric wire 27 having a length exceeding that of the electrolytic bath in the electrolyte.

When the apparatus is adapted to simultaneously measure the sectional area ratio and polish the electric wire, it is conceivably preferable to mount a mechanism for feeding back wire diameter data measured after dissolution and correcting the amount of dissolution.

The electropolishing apparatus having the aforementioned structure was employed to uniformalize copper ratios of Cu-covered superconducting wires, for example. Concrete examples are now described.

(EXAMPLE 7)

First, about 8000 hexagonal superconducting single-core wires of 2.55 mm in flat-to-flat distance were charged in a copper pipe of 307 mm in outer diameter and 251 mm in inner diameter to attain a copper ratio 1.38, and the copper pipe was sealed with a copper cover, to prepare a billet. Then, this billet was degressively worked through hot extrusion, to prepare a multicore superconductor of 80 mm$\phi$ in diameter. This superconductor was repeatedly drawn into 2.9 mm$\phi$ in diameter.

The copper skin of the as-obtained superconducting multicore wire was dissolved by electropolishing, and adjusted to attain a copper ratio of 1.25.

Such a method of adjusting a copper ratio by electropolishing is now described in detail with reference to the drawings.

Figure 8:
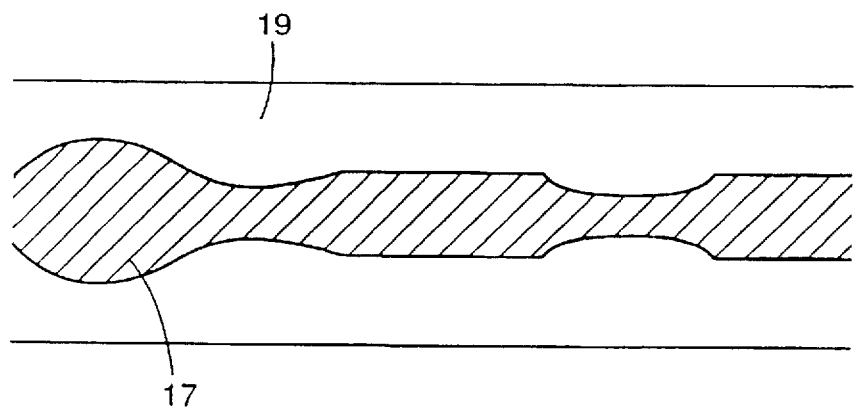
FIGS. 8 to 10 illustrate manufacturing steps for adjusting an electric wire having a dispersed copper ratio to attain a uniform copper ratio by electropolishing.
Figure 9:
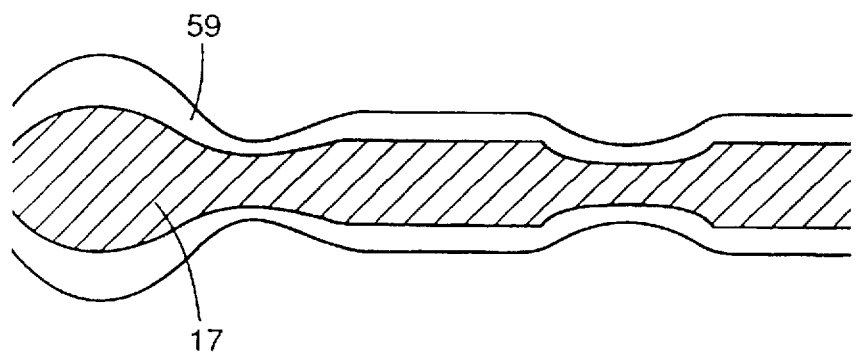
Figure 10:
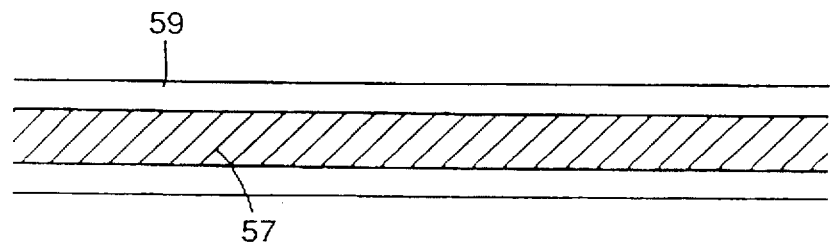

FIGS. 8 to 10 illustrate manufacturing steps for adjusting a superconducting wire having a dispersed copper ratio to attain a uniform copper ratio by electropolishing.

FIG. 8 is a longitudinal sectional view showing a superconducting multicore wire obtained in the aforementioned steps up to wire drawing.

Referring to FIG. 8, this superconducting multicore wire includes a core part 17 consisting of a superconducting material embedded in copper serving as stabilizing material, and a copper skin 19, wherein the sectional area ratio of the core part 17 to the copper skin 19 is not uniform along its longitudinal direction, and as a result, the copper ratio is not uniform either, along the longitudinal direction.

Copper ratio distribution of this superconducting wire was measured along the overall length in a nondestructive manner, as follows:

The superconducting wire was re-wound with a small thickness and a rather short overall length in contact with a four-probe electrode of a proper length, and subjected to measurement of electric resistance. This electric resistance value was converted to a sectional area ratio between the superconducting material part and the copper skin through previously obtained respective electric resistance values thereof. Thus, it was possible to continuously measure copper ratio distribution of the superconducting wire.

More specifically, when the present invention is applied to such a multicore wire, the ratio between the cross section of a portion formed of superconducting material of the core part with respect to the cross section of the portion formed of the stabilizing material of the core part plus that of copper or copper alloy constituting the covering layer can be measured.

Then, the copper skin was dissolved by electropolishing. At this time, relation between the amount of a current applied to the electrolyte, the speed for moving the superconducting wire and the amount of dissolution of copper in the electropolishing was previously obtained. On the basis of this relation, electropolishing was carried out while controlling the amount of the current applied to the electrolyte and the speed for moving the superconducting wire, so that the copper skin was dissolved by a large amount in a portion having a high copper ratio and by a small amount in a portion having a low copper ratio.

FIG. 9 is a longitudinal sectional view showing the superconducting wire which was electropolished in the aforementioned manner.

Referring to FIG. 9, this superconducting multicore wire comprises a core part 17 and a copper skin 19, and its copper ratio is uniformalized along the longitudinal direction.

(COMPARATIVE EXAMPLE 3)

First, about 8000 hexagonal superconducting single-core wires of 2.55 mm in flat-to-flat distance were charged in a copper pipe of 307 mm in outer diameter and 251 mm in inner diameter to attain a copper ratio of 1.25, and the copper pipe was sealed with a copper cover, to prepare a billet. Then, this billet was degressively worked through hot extrusion, to prepare a multicore superconductor of 80 mm$\phi$ in diameter. Then, this superconductor was repeatedly drawn into 2.9 mm$\phi$ in diameter.

Figure 11:
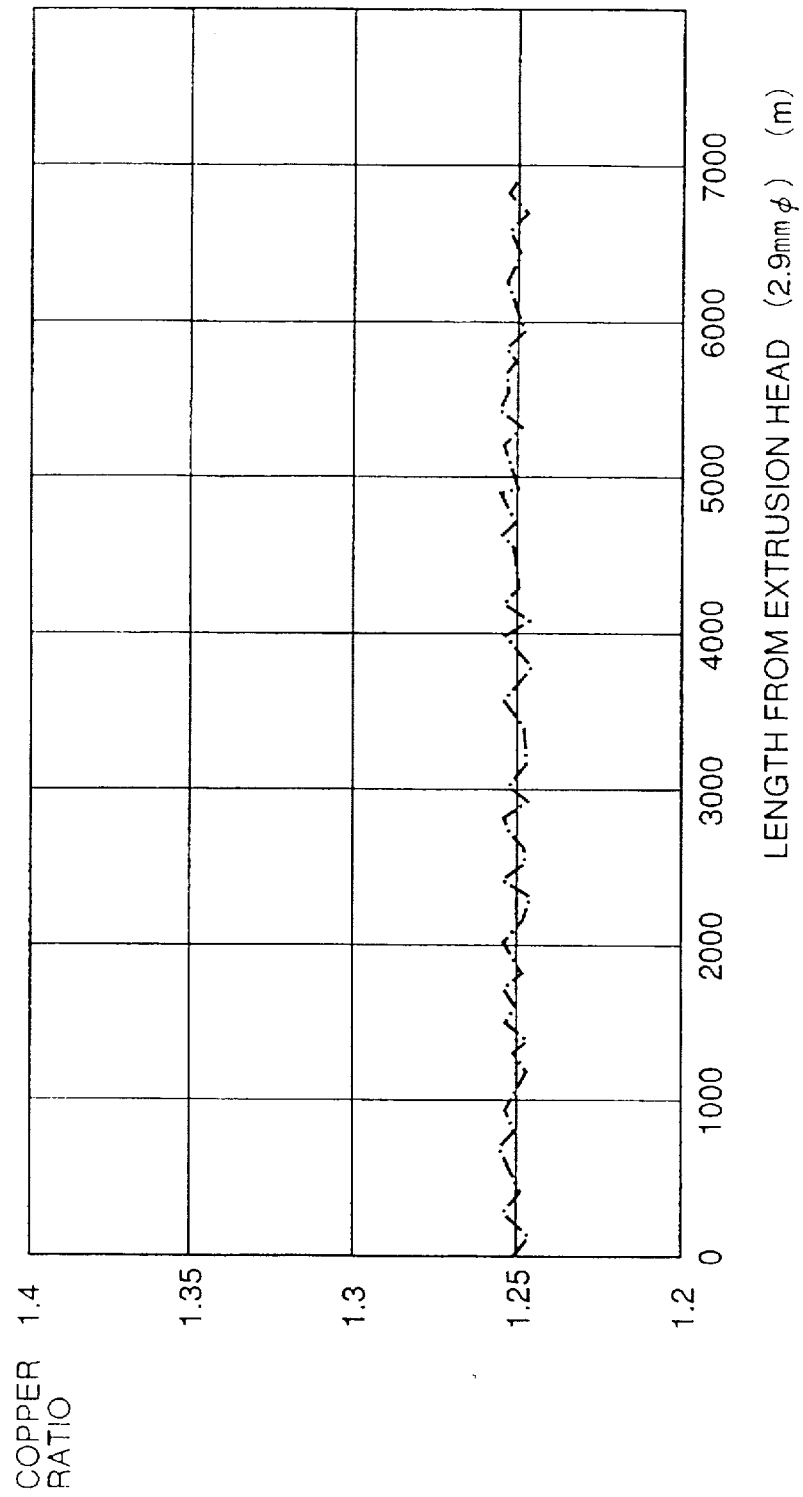
FIG. 11 illustrates exemplary longitudinal copper ratio distribution of a superconducting multicore wire which is uniformalized in longitudinal copper ratio according to the present invention.
Figure 12:
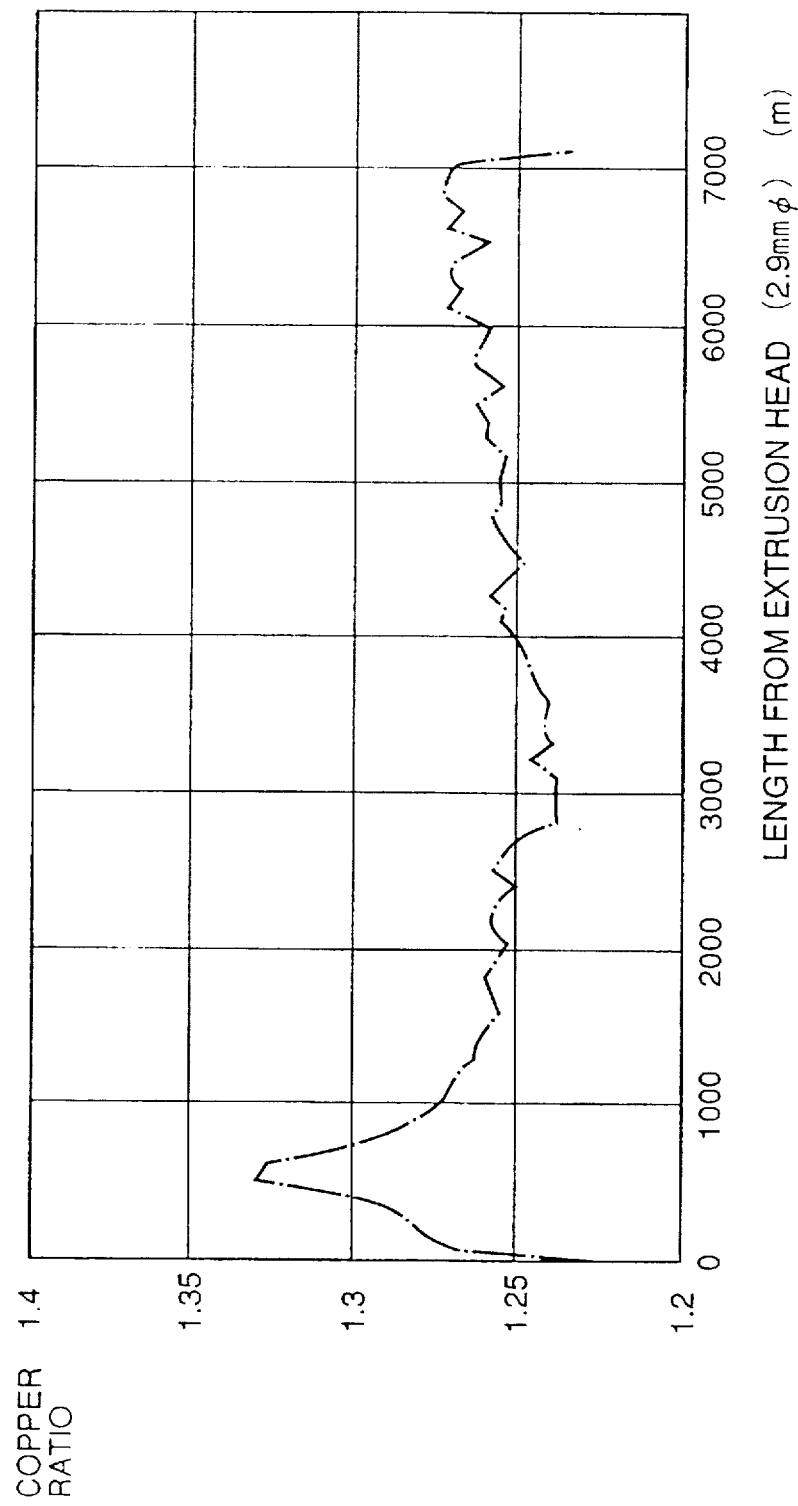
FIG. 12 illustrates exemplary longitudinal copper ratio distribution as to a conventional superconducting multicore wire.
Figure 13:
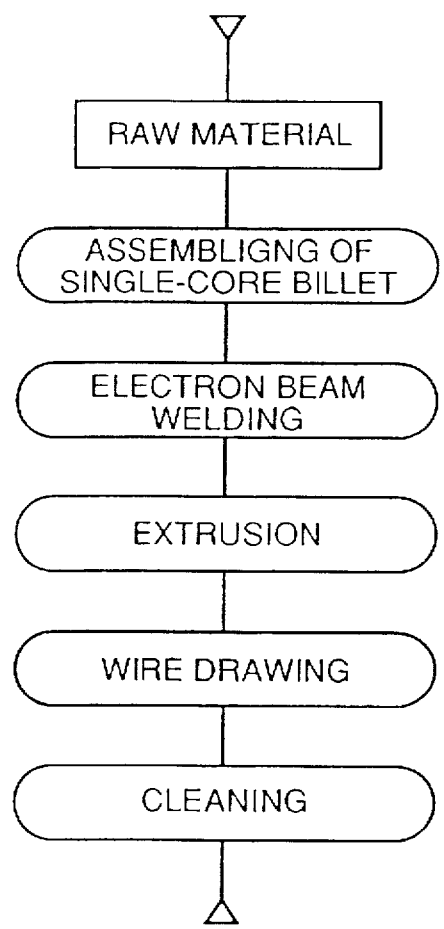
FIG. 13 is a flow chart showing steps of manufacturing a conventional NbTi superconducting single-core wire.
Figure 14:
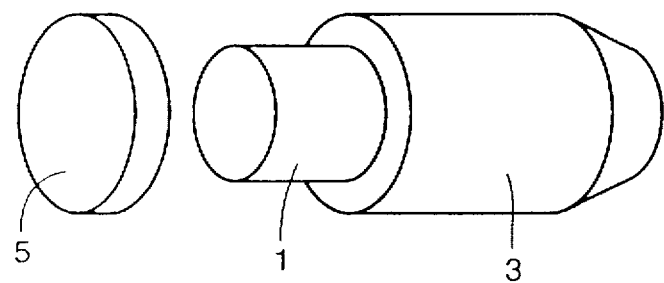
FIGS. 14 to 16 illustrate respective stages in the steps of manufacturing a conventional NbTi superconducting single-core wire.
Figure 15:
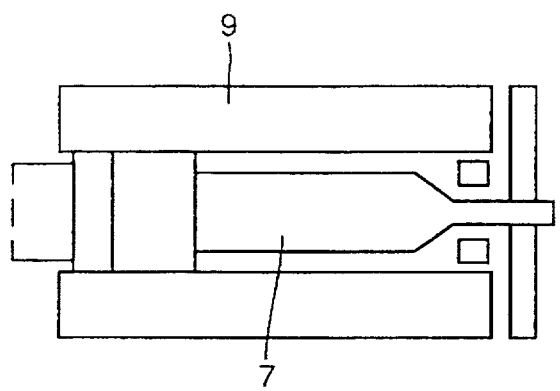
Figure 16:
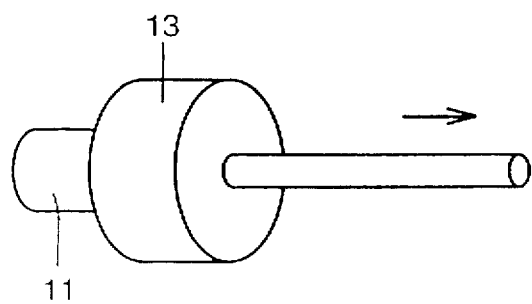
Figure 17:
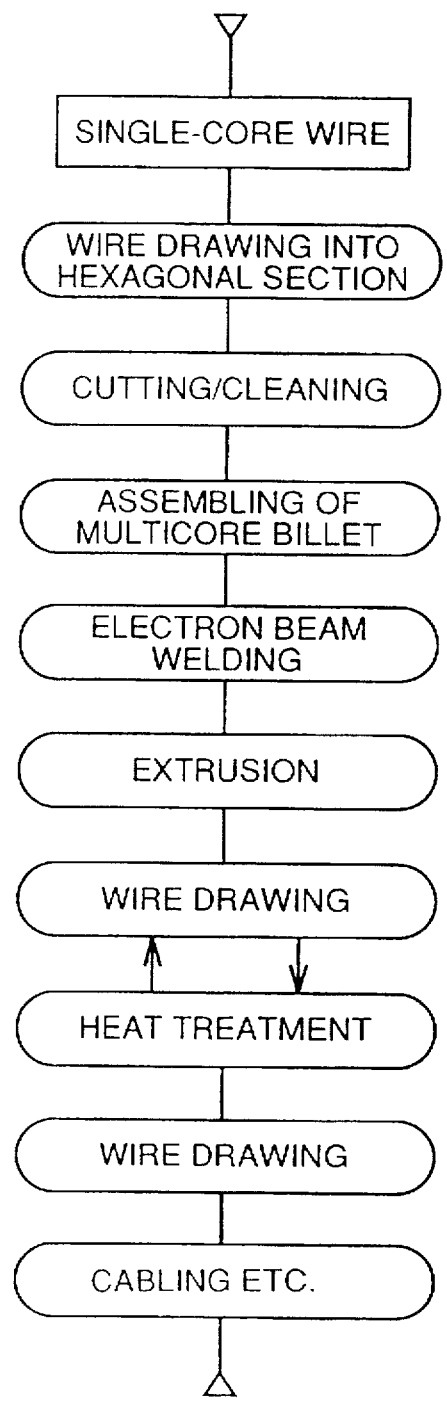
FIG. 17 is a flow chart showing steps of manufacturing a conventional NbTi superconducting multicore wire.
Figure 18:
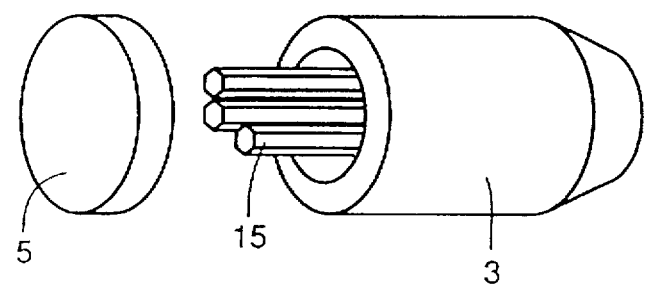
FIG. 18 illustrates a stage in the steps of manufacturing a conventional NbTi superconducting multicore wire.
Figure 19:
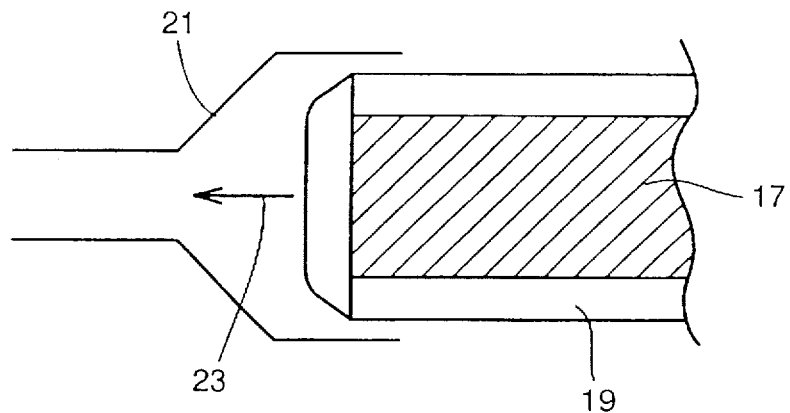
FIGS. 19 to 21 are sectional views showing states of a superconducting wire in extrusion.
Figure 20:
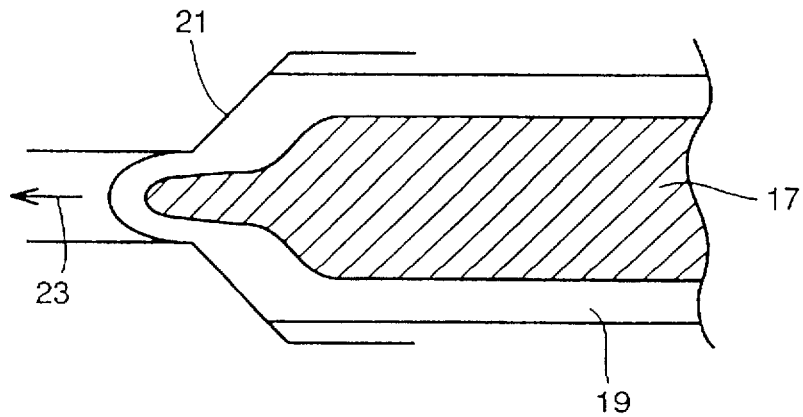
Figure 21:
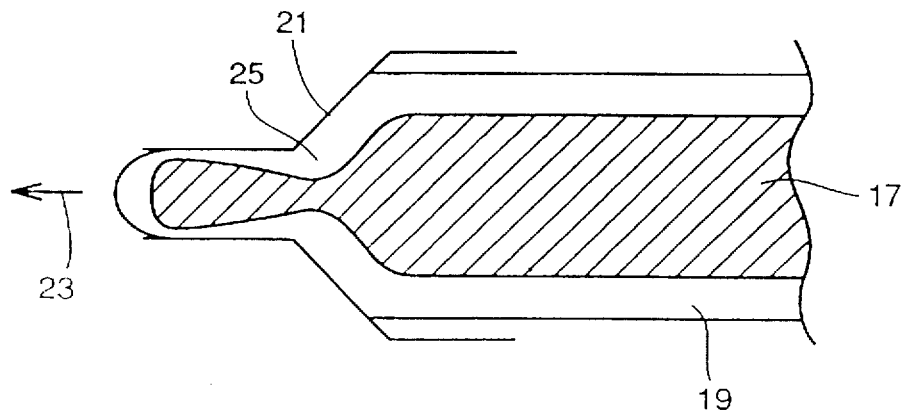
Figure 22:
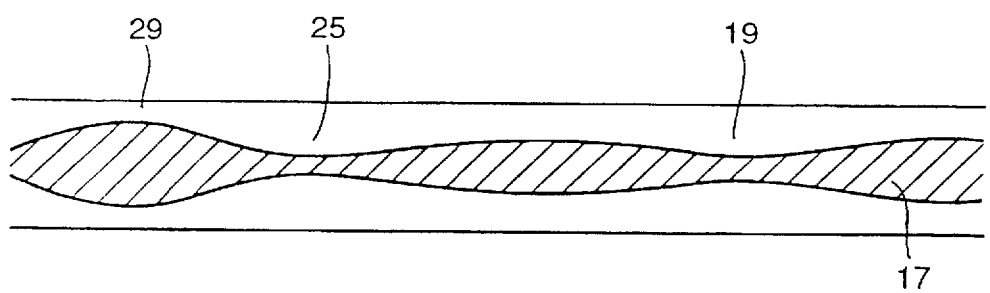
FIG. 22 is a longitudinal sectional view showing a state of a conventional superconducting wire after extrusion.

Final copper ratio distribution states of the as-prepared superconducting multicore wires of Example 7 and comparative example 3 were measured. FIGS. 11 and 12 show the results.

FIG. 11 illustrates longitudinal copper ratio distribution in the superconducting multicore wire of Example 7. FIG. 12 illustrates longitudinal copper ratio distribution in the superconducting multicore wire of comparative example 3. Referring to each of FIGS. 11 and 12, the axis of abscissas shows a length (m) from a head after hot extrusion to the diameter of 2.9 mm$\phi$, and the axis of ordinates shows the copper ratio.

From the results of measurement, maximum, minimum and average values of copper ratio distribution were obtained in the superconducting multicore wires of Example 7 and comparative example 3. Table 1 shows the results.

TABLE 1

|  | Example | Comparative Example |
|---|---|---|
| Target Copper Ratio | 1.250 | 1.250 |
| Maximum Value | 1.256 | 1.329 |
| Minimum Value | 1.244 | 1.215 |
| Average Value | 1.250 | 1.260 |
| Standard Deviation/ Average Value | 0.004 | 0.014 |

It is clearly understood from FIGS. 11 and 12 and Table 1 that the superconducting multicore wire according to Example 7 has extremely uniform copper ratio distribution as compared with the superconducting multicore wire of comparative example 3.

When the copper ratio is adjusted by electropolishing in the aforementioned manner, it is preferable to set an amount of copper diffusion so that the wire diameter of a superconducting wire having a wire diameter of about 1 to 4 mm is reduced by about 1 to 200 μm, in consideration of efficiency.

(EXAMPLE 8)

The wire diameter of the superconducting multicore wire according to Example 7 whose copper ratio was adjusted by electropolishing was dispersed between 2.78 mm and 2.91 mm.

2500 m of such a superconducting multicore wire having a dispersed wire diameter was again drawn through a die series having a degressive ratio of 18%.

FIG. 10 is a longitudinal sectional view showing the as-drawn superconducting wire.

Referring to FIG. 10, this superconducting multicore wire comprises a core part 57 and a copper skin 59, with a copper ratio and a wire diameter which are uniformalized along the longitudinal direction.

(EXAMPLE 9)

2500 m of the superconducting multicore wire of Example 7 having a dispersed wire diameter as described above was again drawn through a die series having a degressive ratio of 80%.

As to the superconducting multicore wires of Examples 8 and 9 prepared in the aforementioned manners, frequencies of wire breaking during the working were examined. Table 2 shows the results.

TABLE 2

| Wire-Drawn Diameter | Example 8 (Degressive Ratio 18%) | Comparative Example 9 (Degressive Ratio 30%) |
|---|---|---|
| to 2.5 mm | 0 | 1 |
| to 2.0 mm | 0 | 3 |
| to 1.5 mm | 0 | 18 |
| to 1.0 mm | 1 | Undrawable |
| to 0.8 mm | 2 | Undrawable |

It is clearly understood from Table 2 that the superconducting wire of Example 8 has a smaller frequency of wire breaking and superior drawability as compared with that of Example 9.

Thus, it is conceivably preferable to bring the degressive ratio of a die to 10 to 25% for re-drawing a superconducting wire whose copper ratio is adjusted by electropolishing to attain a uniform wire diameter, in order to prevent the skin of copper or a copper alloy from rearward flow and to prevent wire breaking.

(EXAMPLE 10)

When the copper ratio of the superconducting multicore wire of Example 7 was adjusted by electropolishing, the surface current density of the superconducting multicore wire was set at 100 A/dm$^2$, to dissolve the copper skin on its surface.

(EXAMPLE 11)

When the copper ratio of the superconducting multicore wire of Example 7 was adjusted by electropolishing, the surface current density of the superconducting multicore wire was set at 300 A/dm$^2$, to dissolve the copper skin on its surface.

The as-prepared superconducting multicore wires of Examples 10 and 11 were compared with each other. As the result, the superconducting multicore wire of Example 10 had an extremely smooth surface after copper dissolution. In the superconducting multicore wire of Example 11, on the other hand, large amounts of molten metal creases and blowholes were caused since the surface current density of the superconducting wire was too high in electropolishing.

Thus, it is conceivably preferable to bring the surface current density of the superconducting wire into 1 to 200 A/dm$^2$, when electropolishing is carried out to adjust the copper ratio.

As hereinabove described, the superconducting wire manufactured according to the present invention is ensured in copper ratio uniformity along its longitudinal direction. Thus, the yield in manufacturing is improved and reduction in cost can be expected. According to the present invention, further, the wire diameter of the superconductor having a uniformalized copper ratio can also be uniformalized by further wire drawing, to obtain a high-performance superconducting wire.

The electropolishing apparatus is widely applicable not only to a Cu-covered superconducting wire but for uniformalizing a sectional area ratio between a core part and a metal covering layer of a metal-covered electric wire having the core part and the metal covering layer covering this core part along its longitudinal direction.

In this case, the covering layer to which the present invention is applicable is conceivably prepared from a material having excellent electric conductivity such as zinc, aluminum, gold, silver, chromium, tin, tungsten, iron, copper or nickel. This is because a certain degree of surface current density is required for electropolishing, and a material having inferior electric conductivity may lead to heat generation at this time.

The electrolyte, which is varied with compatibility with the metal to be dissolved, may conceivably be prepared from acid such as perchloric acid, phosphoric acid, sulfuric acid, chromic acid, nitric acid, sodium hydroxide, potassium hydroxide, cyan or the like. Acid such as phosphoric acid or sulfuric acid is preferable for dissolving copper, for example.

Further, the electropolishing step may be carried out in any stage in the steps of manufacturing a metal-covered electric wire. However, it is necessary to again draw the wire in order to regulate its wire diameter.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for uniformalizing a sectional area ratio between a first material part and a second material part of a metal-covered electric wire having a core part including said first material and a metal covering layer formed of said second material covering said core part along its longitudinal direction, said apparatus comprising:

means for previously storing electric resistance values of said first and second materials respectively;

a pair of first electrodes for feeding a current to a prescribed length region of said metal-covered electric wire;

a pair of second electrodes being placed inside said pair of first electrodes for measuring a voltage being developed in said prescribed length region of said metal-covered electric wire;

means for calculating electric resistance of said metal-covered electric wire in said prescribed length region on the basis of as-applied said current value and as-measured said voltage value;

means for calculating a sectional area ratio between said first material part and said second material part in said prescribed length region on the basis of previously stored said electric resistance values of said first and second materials and actually measured/calculated said electric resistance of said metal-covered electric wire;

an electrolytic bath adapted to contain electrolytic cell;

means for anodizing said electric wire;

a metal member being arranged in said electrolytic bath for serving as a cathode;

means for causing potential difference between said electric wire and said metal member for dissolving a surface layer part of said electric wire by electropolishing;

means for continuously moving said electric wire along its longitudinal direction for continuously passing the same through said electrolytic bath in continuation to said measurement of said sectional area ratio; and means for controlling the amount of dissolution of said surface layer part of said electric wire in response to the result of said measurement of said sectional area ratio.

* * * * *